(12) United States Patent
 Akridge

(10) Patent No.: US 8,530,484 B2
(45) Date of Patent: Sep. 10, 2013

(54) METHOD AND KIT FOR TREATMENT/PREVENTION OF HAIR LOSS

(75) Inventor: Robert E Akridge, Seattle, WA (US)

(73) Assignee: Loreal SA, Paris (FR)

( * ) Notice: Subject to any disclaimer, the term of this patent is extended or adjusted under 35 U.S.C. 154(b) by 0 days.

(21) Appl. No.: 12/612,313

(22) Filed: Nov. 4, 2009

(65) Prior Publication Data

US 2010/0166798 A1    Jul. 1, 2010

Related U.S. Application Data

(62) Division of application No. 11/531,488, filed on Sep. 13, 2006.

(51) Int. Cl.
 *A01N 43/90* (2006.01)
 *A61K 31/522* (2006.01)

(52) U.S. Cl.
 USPC ....... 514/263.3; 514/50; 514/120; 514/263.4; 424/231.1

(58) Field of Classification Search
 None
 See application file for complete search history.

(56) References Cited

U.S. PATENT DOCUMENTS

| | | | | |
|---|---|---|---|---|
| 4,946,678 A | * | 8/1990 | Dodd et al. | 424/581 |
| 6,448,285 B1 | * | 9/2002 | Bernard et al. | 514/419 |
| 2003/0007939 A1 | * | 1/2003 | Murad | 424/61 |

OTHER PUBLICATIONS

Olsen et. al., "Evaluation and treatment of male and female pattern hair loss", J. Am. Acad. Dermatol., 2005, vol. 52, pp. 301-311.*
Shapiro et al "Alopecia areata:diagnosis and management" International Journal of Dermatology, 1999, vol. 35, Suppl. 1, pp. 19-24.).*

* cited by examiner

*Primary Examiner* — Brandon Fetterolf
*Assistant Examiner* — Jean Cornet
(74) *Attorney, Agent, or Firm* — Jensen & Puntigam, P.S.

(57) ABSTRACT

The method includes the steps of cleansing of the scalp sufficiently to remove material which would otherwise block antiviral medication from reaching hair follicles, heating the scalp to increase the absorption of the antiviral medication and applying the antiviral medication to the scalp in effective amount to suppress viral replication or viral activation present in the nerves leading to the scalp.

7 Claims, 2 Drawing Sheets

| Sex | HSV-1 Before Puberty | Genetically Predisposed To Convert More DHT | HSV-1 After Puberty | Will Become Bald |
|---|---|---|---|---|
| Female | + | N/A | | - |
| Female | - | N/A | + | - |
| Male | + | + | | ++ |
| Male | + | - | | - |
| Male | - | + | | - |
| Male | - | + | + | +/- |
| Male | - | - | | - | form
METHOD AND KIT FOR TREATMENT/PREVENTION OF HAIR LOSS

PRIOR APPLICATION

This is a divisional application of U.S. patent application Ser. No. 11/531,488 filed Sep. 13, 2006 and claims the priority thereof.

TECHNICAL FIELD

This invention relates generally to the field of hair loss and, more specifically, concerns a method and related kit for use in the treatment and/or prevention of hair loss.

BACKGROUND OF THE INVENTION

Hair loss, although not a life-threatening or physically painful condition, does have significant negative social and psychological effects. In the United States, approximately 35 million men younger than 50 have discernable hair loss, and considerable effort and expense are incurred in attempts to remedy the condition. The demand for hair loss/regrowth treatment is a multibillion dollar industry. This includes various treatments, including treatment products, as well as surgical procedures for hair restoration, such as hair transplants. While a hair transplant process can be effective, it is also quite expensive, and takes considerable time to produce the desired results. Other techniques, such as hair weaving, also exist.

There are a wide variety of hair loss treatment products; most of them, however, have no positive effect at all. Two products approved by the FDA have shown some results (Finasteride and Minoxidil). However, these products do not work for all users, in particular those that already have significant hair loss, and the improvement is relatively small for most consumers. Further, improvement is lost if the required topical application or oral treatment is stopped.

Since hair loss does have a significant negative effect on many individuals and since the problem is quite widespread, it would be desirable to have a treatment which is effective in preventing hair loss or stimulating regrowth, while being relatively inexpensive and not requiring a surgical procedure.

DISCLOSURE OF THE INVENTION

Accordingly, one embodiment is a method for treatment/prevention of hair loss, comprising the steps of: cleansing the scalp sufficiently to remove material which would block an antiviral agent from reaching the hair follicles; heating the scalp so as to increase absorption of antiviral agent applied to the scalp; and applying an antiviral agent to the scalp in an effective amount to suppress viral replication or viral activation present in the nerves in the region of the scalp which lead to hair loss.

BEST MODE FOR CARRYING OUT THE INVENTION

This invention is directed toward a method and an accompanying kit for treatment or prevention of hair loss. The method and kit are based on a new understanding of the possible cause of hair loss set forth in this application. It is currently believed that hair loss is the result of a genetic link. Those who have the specified genetic factor have a predisposition for increased conversion of testosterone to dihydrotestosterone (DHT), caused by too much of a particular enzyme, 5-alpha reductase, which converts testosterone to DHT. DHT is thought to be the actual cause of hair loss, by accelerating the hair growth cycle, preventing new hair from maturing and producing an early fallout of existing hair. Over time, the hair follicles (cells) weaken and die.

Figure 1:
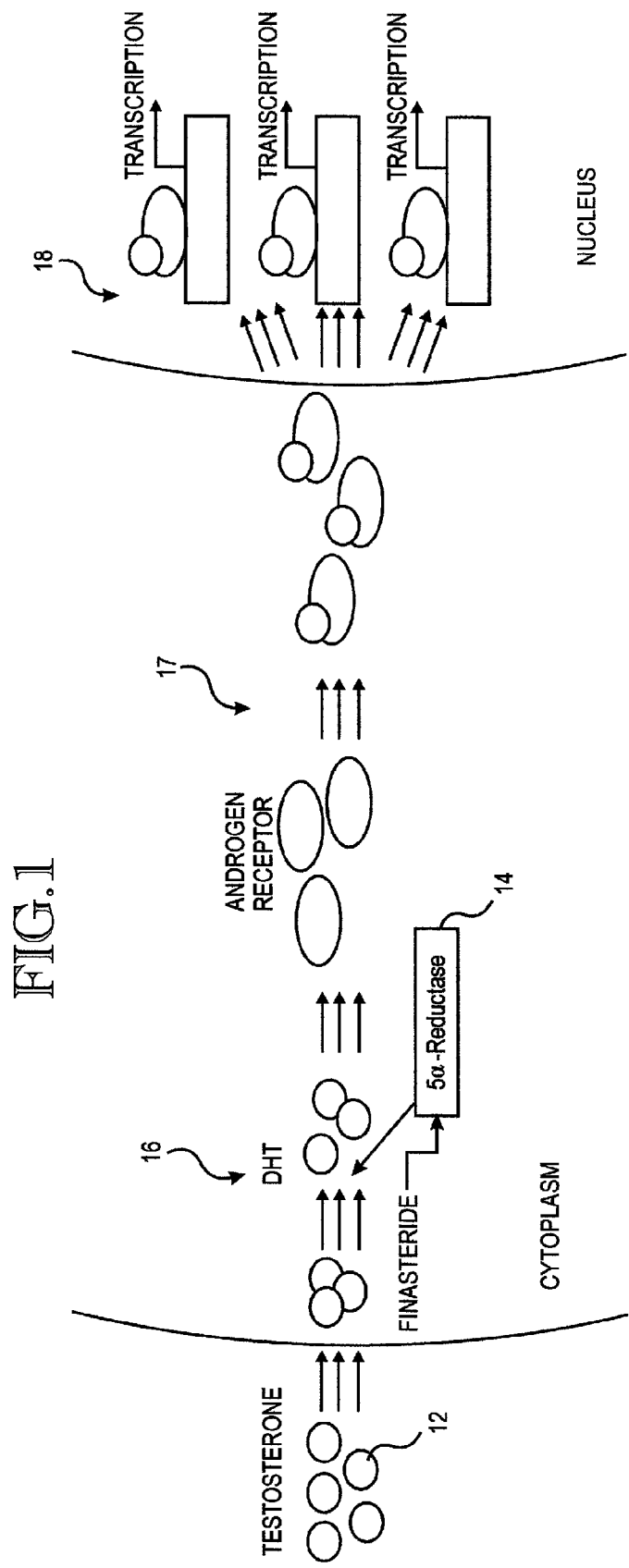
FIG. 1 is a diagram illustrating the cause of hair loss as currently understood (prior art).

One product approved by the FDA currently available for hair loss treatment, Finasteride (Propecia®), blocks the enzyme 5-alpha reductase, while the other, Minoxidil (Rogaine®), is believed to produce increased blood vessel formation to the hair follicle, thereby preventing the death of the follicle. The process of hair loss as currently understood is illustrated in FIG. 1, in which testosterone 12 is converted by the enzyme 5-alpha reductase 14, to DHT 16. The androgen receptor 17 for the DHT 16 with its transcription effect relative to the hair follicle in the nucleus 18 of the cell causes the hair loss. In FIG. 1, the use of Finasteride 19 blocks the effect of 5-alpha reductase.

In the new understanding of hair loss, disclosed herein, the underlying cause of hair loss is quite different, although DHT still plays a role. In this new concept, a virus dwelling in the nerves of the scalp, and the human body's response to the virus, results in male pattern baldness. More specifically, the cause of hair loss is the result of an initial chronic viral infection which comes to dwell in the nerves of the scalp, followed by activation of latent viral replication and viral release, followed in turn by an immune response to the virus and/or mimicked viral components, with resulting elevated levels of DHT further stimulating the viral replication and producing an antiviral immune response which weakens the hairs, resulting in fallout. Thus, in virally infected males, the conversion of testosterone to DHT increases viral replication whenever viral latency is broken, producing continuing action against hair follicles.

Baldness and the degree of baldness is further indicated as being linked to viral acquisition prior to puberty. Once puberty occurs, elevated levels of testosterone in males is normally converted to DHT. Under the new concept described herein, men who are predisposed to convert testosterone to elevated levels of DHT actually only become bald if they are also infected with a virus which dwells in the nerves of the scalp. Baldness is hence limited to the areas serviced by nerves and nerve branches where the latent virus resides. In summary, baldness is caused by a chronic viral infection, its future replication at some point in time and the associating immune response of the body to the virus and/or mimicked viral components.

The chronic viral infection can be the result of various known viruses. One strong possibility is the herpes simplex virus-1 (HSV-1), or a mutant form thereof. There are currently nine known herpes viruses, two of the best known and most prevalent of which are HSV-1 and HSV-2. HSV-1 ("the kissing virus") is typically transmitted by oral contact (such as a kiss on the lips). Transmission usually occurs in childhood by contact with an adult with an oral lesion. After infection, the virus is usually latent in the nerves and only replicates when the latency is broken. In the United States, by teenage years or young adulthood, about 50 percent of Americans have HSV-1 antibodies in their blood. By the time they are over age 50, approximately 80 to 90 percent have HSV-1 antibodies. In other countries, particularly Asian countries, HSV-1 antibodies are much less prevalent, as is the rate of baldness. HSV-2, also known as genital herpes, is also a virus which can have the same effect for baldness.

Figures 2, 3:
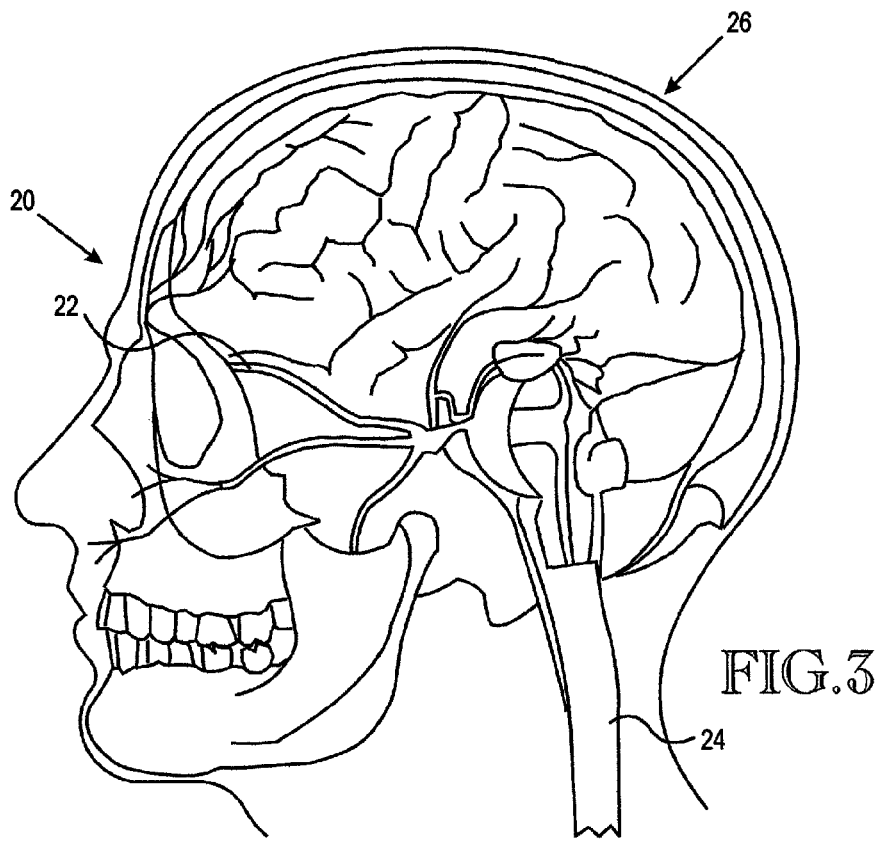
FIG. 2 is a chart illustrating the potential for baldness based on the causes of baldness discussed herein.
FIG. 3 is an illustration of the human skull and the pattern of nerves over the skull area.

HSV is sequestered in specific nerves of the nervous system, including the nerves to the scalp. The virus residing in the nerves affecting the scalp produce the effect of baldness. Male pattern baldness is caused by viral replication on the specific nerves which are directed to the top of the head. Referring to FIG. 3, showing a skull 20, particular nerves 22 which extend from the spinal column 24 to the top and crown of the head 26 is a common location for a resident HSV-1 virus. The nerves that feed the hair on other areas of the head, such as the side and rear, are from different main nerves. Those nerves are typically unaffected by a baldness-producing virus. Accordingly, the sides and back of heads of men with pattern baldness tend to have hair, because the nerves to those areas are unaffected by viruses. This is in opposition to the current theory, which states that those areas have hair which is resistant to DHT.

Thus, baldness patterns are viewed as a reflection of a neurological (nerve) pattern (the nerves being affected by a virus), as opposed to a pattern of DHT resistance. Typically, balding which starts out at the rear top of the head is due to the virus initially taking the path of least resistance, exiting at the nerve endings at that particular location.

It is the combination of a virus in specific nerves to the scalp, and a genetic predisposition to convert more testosterone into DHT, which accounts for male pattern baldness. The degree of baldness is linked to viral acquisition prior to puberty, since hair loss will begin as elevated testosterone begins at puberty, with conversion to DHT. Note from the table of FIG. 2, that a male (females do not become bald under this viral infection theory because testosterone in the scalp is lacking and therefore not converted to DHT) who is infected with HSV-1 before puberty, as well as being genetically predisposed to a high concentration of DHT, will certainly (++) become bald. Before puberty, the virus previously transmitted is latent in specific nerves in the scalp area, and only becomes active as a result of the increase in testosterone following puberty, when normal latency of the virus is broken. As further indicated in the table, if exposure to the virus occurs after puberty, those individuals will lose their hair but at a different rate or in a different pattern than otherwise. The table further indicates that unless both factors are present, the individual will not lose hair in male pattern baldness.

The treatment set forth herein is based in a primary embodiment on medications used to treat viral infections, in one example, medications for treatment of herpes. Herpes medications include Acyclovir (Zovirax), Valacyclovir (Valtrex), Famciclovir (Famvir) and Trifluridine (used for HSV eye infections). In one aspect of the present invention, the antiviral medication is applied topically in a way as to penetrate the skin and reach the hair follicles. Typically, even though an individual has been exposed in pre-puberty to viral infection, treatment will not begin at that point. However, post-puberty, in young males, with initial loss of hair, one phase of the treatment will include a topical application of an antiviral medication. This can also be used at a later time, even when hair loss is more advanced.

The preferred method includes a first step of cleansing the scalp. An acidic shampoo, like glycolic acid, citric acid, or other hydroxyl or beta-hydroxyl acid is used to clean the scalp. The shampoo should be applied using a skin care brush or cleanser with an abrasive scrub element. One example of a suitable power skin brush is shown in U.S. patent application Ser. No. 10/873,564 and Ser. No. 10/873,584 which are owned by the applicant of the present invention. However, other brushes having a similar scrubbing effect can be used.

In the next step, the scalp is prepared to absorb the medication, assuming the shampoo has been effective in the cleansing of the scalp. Immediately after the scalp has been cleaned, with the follicles thus being free of debris, the skin care brush is used to apply warm water for ten to 60 seconds. Heat helps in increasing absorption of the viral medication.

The medication is then applied in an amount on the prepared scalp to cover the hair loss area with a visible amount of medication, using a damp warm brush or an applicator. The material is placed on the balding area with gentle pressure, using the brushhead applicator. A circular motion is appropriate, with 10 to 60 seconds of application. The medication is then applied a second time, using the applicator, allowing the topical medication to be absorbed into the skin. This procedure can be carried out both in the morning and before bedtime.

The antiviral medication itself can be in the form of lotions, creams, solutions, patches, or other drug formulations. The active ingredient must be a drug or combination of drugs which is known to be antiviral or to suppress viral replication. These include the medications mentioned above, specifically Acyclovir, Valacyclovir, Famciclovir and others, including Penciclovir, and Doscosanol. Still other medications are possible.

In the event that hair loss continues, it is possible, even likely, that the hair follicles are plugged, preventing the absorption of an appropriate amount of medication. In such a case, treatment should include using an abrasive cleanser with a skin care brush, or chemically peeling the scalp using conventional over the counter (OTC) skin peels or removal of the plugs using adhesive skin strips or the like.

The scalp can also be further prepared with heat to absorb the medication. Other heat techniques can be used, including covering of the bald area with a plastic wrap, adding a hot wet towel for five minutes or so, with the topical medication being then applied with a skin care brush. Alternatively, dry heat from a hair dryer or the like can be used to heat the skin for two minutes or so prior to applying the medication with the skin care brush.

In addition to the topical treatment, a systemic treatment plan can also be used. The status of the virus can be maintained at a low level on the basis of oral antivirals. This can be used alone, or combined with the topical treatment for maximum effectiveness. An initial suppression of the virus can be treated using the above medications, specifically Acyclovir, Famciclovir, and Valacyclovir. Other medications can be used as they are discovered to be effective against the herpes virus or perhaps other viruses which may be discovered to be a cause of the hair loss. In this regimen, for initial suppression, as an example, Acyclovir can be taken at 400 milligrams three times a day for five days, 200 milligrams five times a day for five days, or 800 milligrams twice a day for five days. Famciclovir can be taken at 125-250 milligrams twice a day for five days; while Valacyclovir can be taken at 500 milligrams—1 milligram twice a day for 3-10 days, or 1 gram once a day for 5 days.

For suppressive therapy to prevent hair loss, possible effective protocols include Acyclovir for 400 milligrams twice a day or Famciclovir 250 milligrams twice a day, or Valacyclovir for 500 milligrams once a day, or further, 1 milligram once a day. The above are examples of possible medications and the level of medications necessary to produce the desired response. Finally, intravenous administration of medications, such as Foscarnet, for Acyclovir-resistant herpes can be used, in a hospital or supervised at-home situation.

It should be understood that the above medications can be used alone or in some combination, in addition to other antiviral medications.

In addition to the antiviral medications disclosed above, other viral therapies are known which could also be used for the suppression or prevention of the viral infection, which will result in fewer viral particles and a suppressed imunoresponse to the virus and/or mimicked antiviral antigens.

One example of such an antiviral therapy is vaccination. The vaccine would result in the prevention of the transmission of the virus so as to prevent hair loss. Hence, vaccine therapy could be effective in this application.

Another effective therapy is known as photodynamic therapy (PDT). PDT involves the use of light of a specific wave length in conjunction with a chemical reagent. When a specific wave length of light applied to the area coded or embedded with reagent, heightened reaction occurs. This heightened reaction often results in the death of whatever has absorbed the reagent. The use of specific dyes and wave lengths can be used to inactivate herpes virus (for instance) associated with hair loss. As an example, such a dye could be applied to the scalp of the head, enabled to penetrate to the appropriate depth of the hair follicle, and then exposed to a given effective wavelength, so as to inactivate the virus or force it back into latency.

Another example is the use of topical chemicals. For instance, a simple chemical element or chemical compound could inactivate, suppress or block the suspect virus in a specific location, resulting in diminished hair loss. In addition to the light-activated chemicals mentioned above, some chemicals when exposed to air or a correct enzyme result in an increase in temperature, e.g. sufficient to impact the virus. These simple chemicals, dyes or forms of iodine, could have enough of an effect on viruses by themselves to prevent or reduce the damage to hair follicles.

Still further, it is commonly known that heat can inactivate pathogens and prevent disease or help accelerate the immune response to a given pathogen. By accelerating the healing rate using heat, it is possible that the level of virus present is reduced over a given time, resulting in a suboptimal viremia to also trigger an immune response significant enough to result in hair loss. Heating could be applied to the scalp for a specified time, causing the virus to retreat into a latent state and reduce or quiet the immune response so as to prevent the destruction of the hair.

As a group, the above are referred to as antiviral agents.

Still other viral treatments may be possible. The above illustrate various possible treatments to counteract or reduce the viral effect in the nerves of the scalp.

Hence, a discovery has been made relative to cause of hair loss, and a method of treatment and a kit for carrying out the treatment have been disclosed for treating hair loss in accordance with this new discovery.

Although a preferred embodiment of the invention has been disclosed for purpose of illustration, it should be understood that various changes and substitutions can be made to the embodiment without departing from the spirit of the invention, which is defined by the claims which follow.

What is claimed is:

1. A method for treatment of hair loss, comprising the steps of:

cleansing the scalp sufficiently to remove material which would block a HSV medication from reaching the hair follicles, using at least one of the following: (1) a cleansing formulation or shampoo applied with a skin care brush, (2) a chemical peel of the scalp, or (3) adhesive skin strips to remove material from the hair follicles;

heating the scalp so as to increase absorption of an HSV medication applied to the scalp; and applying an HSV medication to the scalp so as to penetrate the skin and reach hair follicles, in an effective amount to suppress viral replication or viral activation present on the nerves in the region of the scalp which lead to hair loss.

2. The method of claim 1, wherein the HSV is chosen from the group comprising: Acyclovir, Valacyclovir, Famciclovir, Foscarnet, Penciclovir and Trifluridine.

3. The method of claim 1, wherein the step of heating the scalp includes the step of applying warm water for a selected period of time by a power skin care brush.

4. The method of claim 1, wherein the step of heating the scalp includes the step of using dry heated air to heat the skin for at least two minutes.

5. The method of claim 1, wherein the step of applying the HSV medication includes the step of applying the medication with a power skin care brush.

6. The method of claim 1, including repeating the step of applying the HSV medication.

7. The method of claim 1, including the further step of ingesting an effective amount of an HSV medication.

* * * * *